United States Patent [19]

Bernard et al.

[11] 4,250,433
[45] Feb. 10, 1981

[54] VACUO SPARK GENERATOR FOR THE SPECTROGRAPHIC ANALYSIS OF SAMPLES

[75] Inventors: Claude R. Bernard, Longjumeau; Bernard Daigne, Chatillon; Francois Girard, Paris, all of France

[73] Assignee: Office National d'Etudes et de Recherches Aerospatiales, Chatillon, France

[21] Appl. No.: 9,512

[22] Filed: Feb. 5, 1979

[30] Foreign Application Priority Data

Feb. 13, 1978 [FR] France ............................. 78 03968

[51] Int. Cl.³ ............................................. H01J 37/04
[52] U.S. Cl. ............................. 315/335; 313/231.7; 313/237; 315/173; 315/234; 356/313
[58] Field of Search .......... 315/167, 173, 234, 241 R, 315/335; 313/231.7, 237; 356/313

[56] References Cited

U.S. PATENT DOCUMENTS 3,317,786  5/1967  Romand et al. ............. 315/173 X
3,619,062  11/1971  Heres et al. .................... 356/313
4,158,790  6/1979  Sullivan ........................ 313/237 X

FOREIGN PATENT DOCUMENTS 902410  8/1962  United Kingdom .............. 313/231.7

Primary Examiner—Eugene R. LaRoche
Attorney, Agent, or Firm—Kane, Dalsimer, Kane, Sullivan and Kurucz

[57] ABSTRACT

An in vacuo spark generator for the spectral analysis in the ultraviolet of a sample acting as an anode, with a coaxial annular cathode cooperating with the anode and an electrode for the formation of initiation sparks the operative portion of which is disposed opposite the outer side surface of the cathode and set back relative the frontal face of the cathode, the cathode frontal face being rounded and the opposite portions of the cathode and the initiation electrode being provided each with removable snap-rings slightly protruding relative to the body of the cathode and initiation electrode; said snap-rings are housed in a semicircular groove provided in the body of the cathode and the initiation electrode.

14 Claims, 7 Drawing Figures

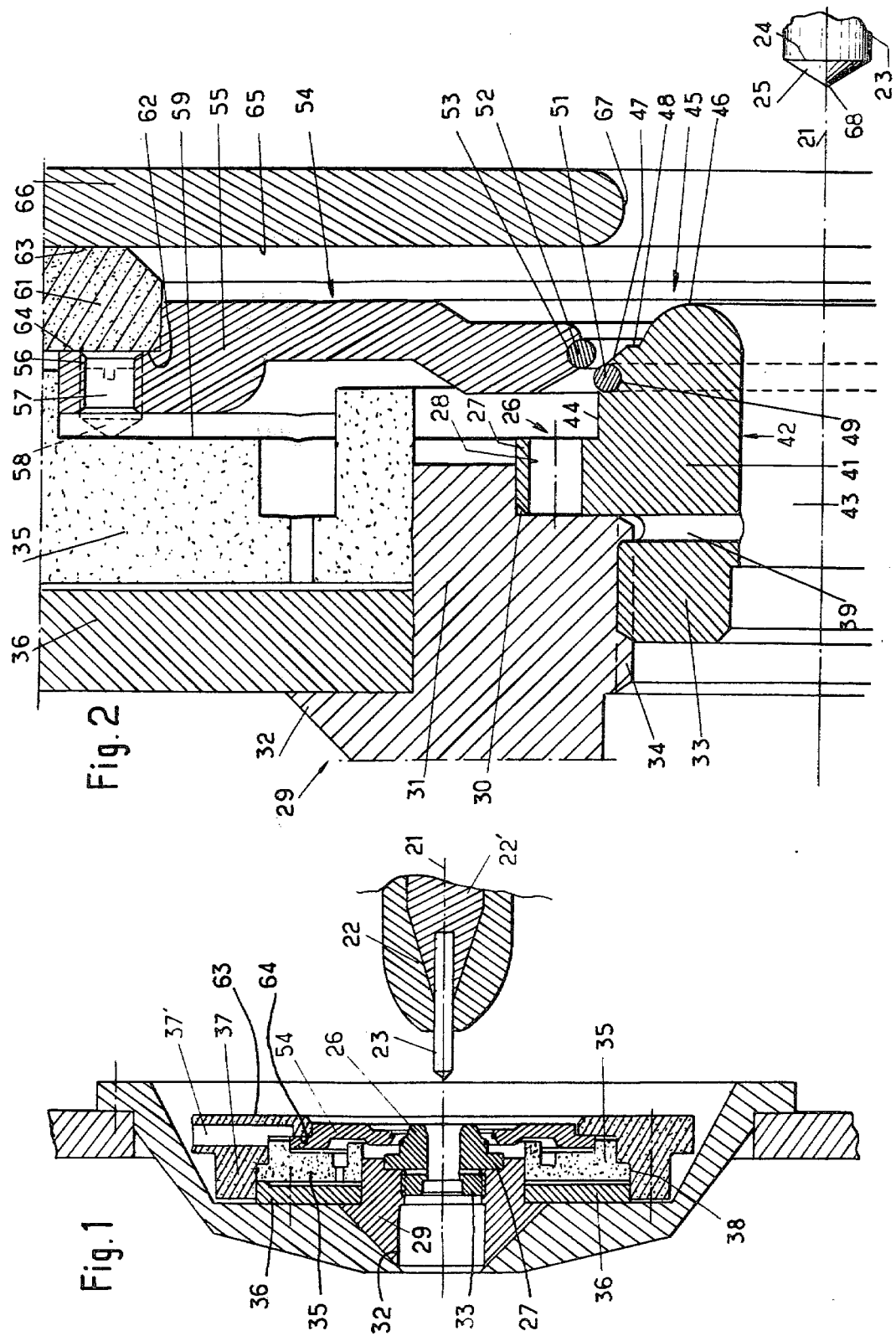

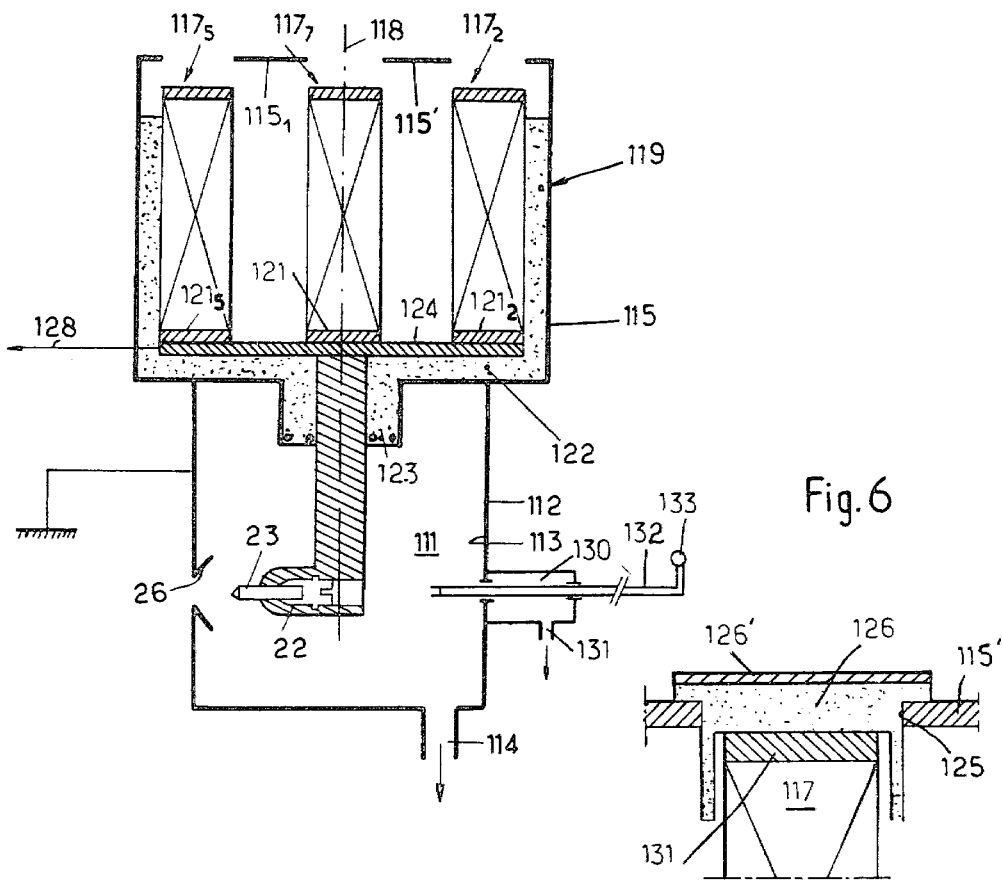
Fig. 4
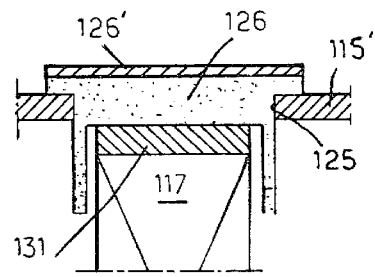
Fig. 6
Fig. 5
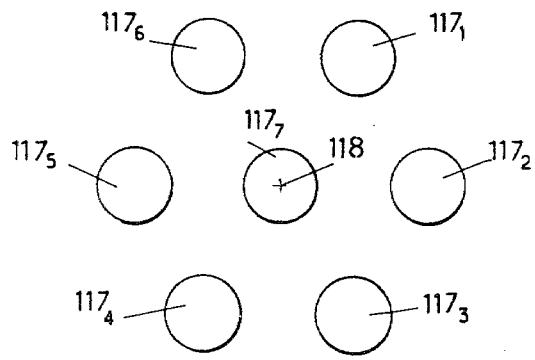
Fig. 7
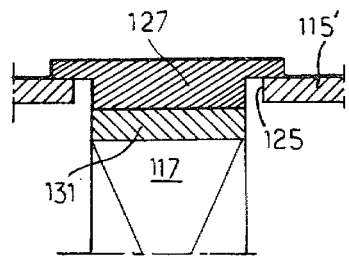

VACUO SPARK GENERATOR FOR THE SPECTROGRAPHIC ANALYSIS OF SAMPLES

BACKGROUND OF THE INVENTION

The invention relates to an in vacuo spark generator for the spectrographic analysis, in the far ultraviolet range, of solid samples.

It is known that the chemical constitution of a sample is determined by the spectrographic study of the plasma formed by which energy electric discharges carried out in vacuo between the sample acting as an electrode and another electrode.

Such discharges are produced by a generator, also called spark source, for exciting a spectral area extending from the far ultraviolet (2000 Å to a few tens of Å) to the vicinity of the weak X-rays.

In order to melt and vaporize by means of an under vacuum spark part of the constituent material of a sample, metallic or not, a considerable energy (from 10 to 100 joules) must be freed during a very short period (from 1 to 10 s). As a result, the analysis conditions quickly deteriorate following wear of the sample and modifications in the physical chemical state of the neighbouring surfaces caused by the extremely high temperature which has developed.

Most of the time, the deterioration is so quick that not only a precise quantitative information is not obtained but that also the results of analyses carried out in succession are not comparable between themselves.

The difficulty increases still more when one attempts to titrate or dose the elements by studying the lines appearing in the far ultraviolet, the energies in action bringing very quickly about a plasma concentration such that the continuous background revealed by the spectrographic analysis quickly masks said lines.

Various types of in vacuo spark generators are known, the differences between them being their principle of operation.

In a first type of generator, so called of the Millikan spark type, the spark is produced in vacuo between two metallic electrodes, one of which being the sample, for a disruptive field of very high value of $10^5$ to $10^6$ volts per cm. For voltages currently used, the distance between the electrodes does not exceed 1 mm. The discharge obtained is poorly stable and difficult to reproduce due to the wear of the electrodes which increases rapidly their spacing. Due to this fact, the generator used for identifying lines of a high ionization degree cannot be used for quantitative analysis.

In a second type of in vacuo spark generator, so-called sliding spark generator, the spark is produced between two electrodes, one of which being the sample, which are in contact with an insulating or semi-conductor support. The disruptive field is from 10 to 20 times weaker than that which is necessary for the generator of the first type and the spark can be formed in vacuo over a length of a few centimeters.

The generator of this second type is used in in vacuo spectrometry for works relating to fundamental research. Due to the insulating support, the generator is not convenient for carrying out quantitative analysis since the insulation supplies its own spectrum in the spectral area of the analysis. Moreover, the development of the spark depends on the physical-chemical nature of the surface of the insulating material, which is modified in permanence due to the thermal effect and to the deposition of material.

In a third type of in vacuo spark generator, so-called initiated spark generator, the main spark produced between two electrodes, one of which being the sample, is initiated by a spark of weaker energy ionizing the medium interposed between the electrodes.

In a first group of generators of this type, used for quantitative analysis in the far ultraviolet spectrum, the initiation spark is a sliding spark. Such apparatuses have the disadvantage mentioned hereabove and inherent to the sliding spark generators: the reproductibility of the discharges is very low. Moreover the maintenance interventions are numerous. In all cases, it is impossible to titrate with such generators the sample elements which are also present in the insulating material, for instance the oxygen of the sample when the insulating material is alumine.

In a second group of generators of this third type, the initiation spark is a Millikan spark, and the object is either to energize the X-radiations (S. K. HÄNDEL in ARKIV FÖR FYSIK-Stockholm 1964), or to obtain continuous spectra in the ultraviolet. The cathode and initiation electrode, placed in the vicinity of each other, are supported by insulators and one observes in the plasma both the spectrum of the sample and that of the insulating material.

SUMMARY OF THE INVENTION

The apparatus according to the invention and intended for the formation in vacuo of sparks between a sample to be analysed, and acting usually as an anode, and another electrode, or cathode, supplies a plasma in which the atoms are energized at levels which are sufficient for providing an analysis in an area of wave-length situated from the near ultraviolet to the far ultraviolet, including the latter, in the vicinity of weak X-rays, with a stability of operation allowing a very accurate quantitative analysis.

The object of the invention is to provide an apparatus free of any insulating material in the vicinity of the area where the plasma is produced, and making use of a main spark initiated by a Millikan spark originating between the cathode and an annular electrode, and it proposes a disposition of the cathode and the initiation electrode allowing a setting up appropriate for the spectrographic analysis in the far ultraviolet in the wave-length range comprised between 2000 Å and a few tens of Å, by providing means allowing carrying out the spectrographic analysis without its results being affected by the presence of the extra electrode and particularly of its insulating support, thus supplying a non polluted plasma the configuration of which is highly favourable for the spectrographic analysis and particularly for the titration of the elements which are present in high proportions or in very small proportions.

The in vacuo spark generator according to the invention, the anode of which is formed by the sample to be analysed, and which comprises an annular cathode as well as, in cooperation with said cathode, an initiation electrode surrounding a portion of said cathode at a small distance from the latter, is characterized in that the auxiliary electrode is sufficiently remote from the frontal face of the cathode so that the plasma formed by the main spark between the sample and the cathode and visible by the spectrograph through the central opening of the latter, cannot be altered by the products resulting from the initiation sparks.

In an embodiment, the cathode is formed with a frontal portion protruding relative to the initiation electrode, the annular gap in which appear the initiation sparks being sufficiently set back relative to said frontal face -the main sparks being formed between said frontal face and the sample-, so that the effects of the initiation sparks have no influence on the constitution of the plasma generated by the main sparks.

In this respect, the invention has for object an embodiment in which the frontal face of the cathode is rounded and substantially toric.

According to a further important feature of the invention, the cooperating areas of the cathode and of the auxiliary electrode for the formation of the initiation sparks are made of a removable snap-ring so that after a certain time of use, it is possible to re-establish the initial conditions for the formation of initiation sparks by replacing the worn out snap-ring by a new one.

The invention has also for object a means for providing the plasma with a favourable configuration for a spectrographic analysis by concentrating said plasma in the central opening of the cathode by use of a fourth electrode, annular, operative by its inner edge and placed in the gap between the sample electrode and the cathode.

The invention has also for object an installation comprising said generator, with means for applying the electric voltages capable of generating the main sparks as well as the initiation sparks, and is characterized in this respect by the relative disposition of the electric components such as to obtain for the assembly a small self inductance value, particularly by providing a battery of capacitors arranged in a closed or co-axial array.

A further object of the invention is the provision of particularly simple means for making operative at will a predetermined number of capacitors.

Finally, the invention has for object to provide means for putting in position and taking away the sample in the in vacuo spark generator.

BRIEF DESCRIPTION OF THE DRAWINGS

The following description which is given only by way of example, refers to the accompanying drawings wherein:

FIG. 1 is a cross-sectional view of a portion of an in vacuo spark generator according to the invention;

FIG. 2 is a larger view, also in cross-section, and showing also a concentration electrode;

FIG. 4 is an axial cross-sectional schematic view of an in vacuo spark generating apparatus;

FIG. 5 is a view defining the position in a plane of the capacitors of the vacuo generator;

FIG. 6 is a partial cross-sectional view of a portion of the apparatus according to FIG. 4;

FIG. 7 is similar to FIG. 6, but for another condition.

DESCRIPTION OF THE INVENTION

Figure 3:
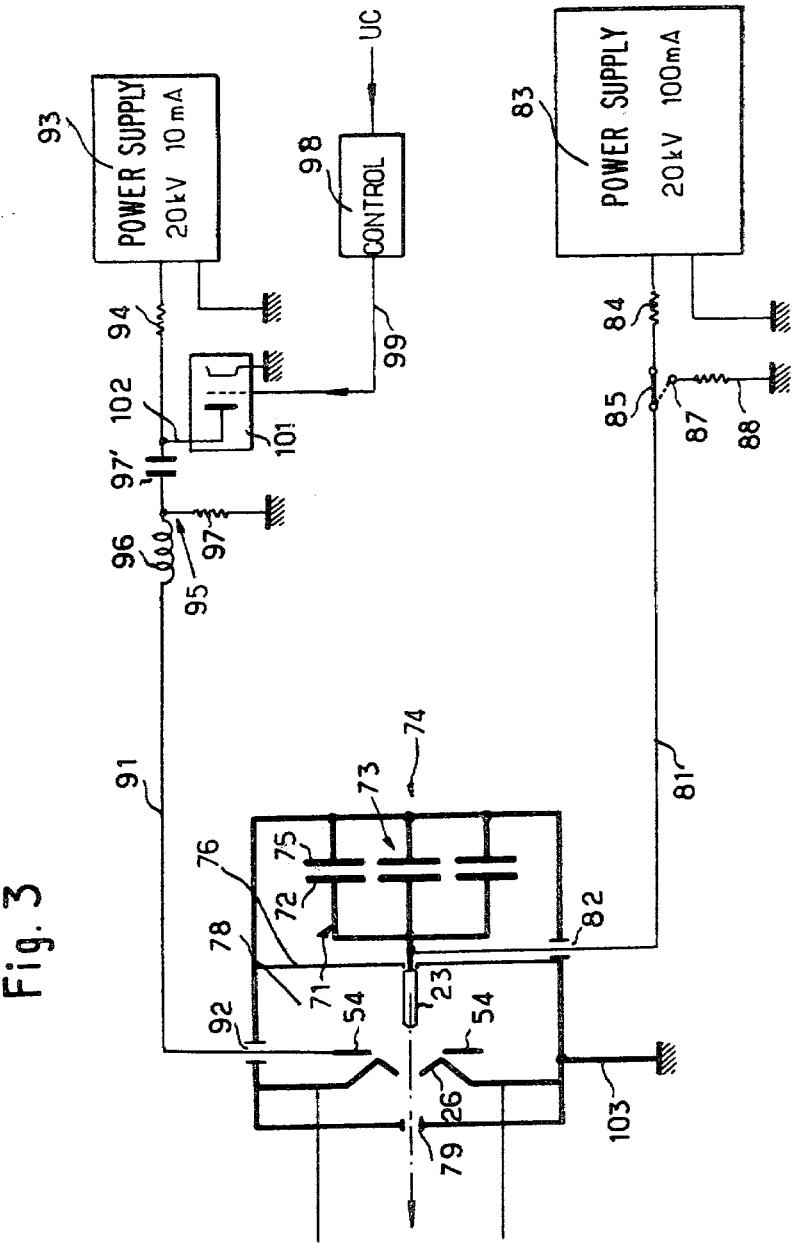
FIG. 3 is an electrical circuit diagram of the in vacuo spark generator.

The electrode device according to the invention comprises, mounted on axis 21 (FIGS. 1 and 2) of a tubular conductive support 22, the sample 23 to be spectrographically analyzed. The end 24 of said sample is cut in the configuration of a cone 25 the apex angle of which is close to 120°. The opposite end of the sample is clamped in a sample-carrier clamp 22' in electrical conductivity relationship with a conductive support 22.

With said sample with acts as an anode, is adapted for cooperation a cathode 26 of general annular configuration, formed with a base 27 having holes 28 provided for its fixation on a cathode support 29. The support 29 made of a thermally conductive material is formed with a cylindrical shaft 31 provided with a step 30 for housing the base 27 and a conical rear protrusion 32. A threaded sleeve 33 forming the rear end of the cathode engages the inner threading 34 of support 29.

The shaft 31 is surrounded over a portion of its height by an insulating circular block 35 maintained between, on the one hand, a metallic disc 36 also threaded onto the shaft 31 and bearing against the annular base of the conical protrusion 32, and, on the other hand, an insulating cover 37 surrounding by its edge 38 the insulating block 35 as well as the disc 36. The insulating cover 37 is formed with a radial passage 37' for an electric conductor the role of which will appear later.

Radial ports 39 emerging in the threading of the sleeve 33 facilitate degassing when creating the vacuum.

The body 41 of cathode 26 from which depends base 27 is bounded by an inner cylindrical surface 42 defining the cathode central opening 43 and by an outer cylindrical surface 44 connected to the foreward frontal face of base 27.

The general shape of the cathode is favourable for obtaining low contact electric resistances and also a good thermal dissipation.

The frontal portion 45 of cathode 26 is limited by a semitoroidal surface 46 connected directly to the inner cylindrical surface 42, and the other end of which is connected to the outer cylindrical surface 44 through an oblique fillet 47 and the shoulder 48. Between the fillet 47 and the cylindrical surface 44 is provided a semi-circular groove 49 adapted for receiving a circular snap-ring 51, advantageously made from a standard refractory metal wire which may be tungsten, molybdenum or niobium.

Opposite snap-ring 51 and separated from the latter by a small gap is a snap-ring 52 which is similar to snap-ring 51 and is housed in a semi-circuar groove 53 having an annular seat (initiation electrode) 54 made of a conductive material, and the outer peripheral edge 55 of which is formed with tapped holes 56, three in number in the example, distributed equi-angularly about axis 21, screws 57 introduced into the holes 56 providing an accurate positioning of seat 54 through the points 58 of said screws coming to bear on the front plane face 59 of the insulating block 35. The immobile fixation of seat 54 is provided by an inner annular protrusion 61 which is part of cover 37 and cooperates with a shoulder 62 of said seat. To seat 54 is connected an electric conductor extending through the insulating cover 57 through passage 37'.

Against face 63 of cover 67 which is opposed to face 64 cooperating with seat 54 is applied the face 65 of a fourth electrode 66 in the shape of a flat ring the inner edge 67 of which is rounded and the apex of which is substantially half-way between the rounded surface 46 of the frontal portion 45 of cathode 26 and the apex 68 of cone 25 of the sample-anode 23.

The sample 23 is connected by circuit 71 (FIG. 3) to the armatures 72 of capacitors 73 forming a battery 74 the other armatures of which are connected with the metallic wall 76 of a chamber 78 gold-plated inside and placed under vacuum, for instance a vacuum of $10^{-7}$ torr and containing the electrodes, said chamber being formed with a slot 79 forming the entrance for a spectrograph.

The circuits 71 are connected through a conductor 81 emerging from chamber 78 through a lead-through 82, with a supply block 83 through a resistor 84. The supply block is for instance at 20 kV and 100 mA. A switch 85 provides at will the grounding of the capacitors through the cooperation of a stud 87 forming the end or terminal of a circuit 88 comprising a resistor.

The initiation electrode 54 is connected through a conductor 91 emerging from chamber 78 through a lead-through 92 with a second supply block 93 at 20 kV and 10 mA with interposition of a resistor 94. A conductor 91 is associated with circuit 95 which includes a coil 96, a resistor 97 and a capacitor 97'.

A control unit UC applies through a checking device 98 an initiation order via a circuit 99 to a thyratron 101 the output 102 of which is connected to conductor 91.

The operation is as follows:

When a signal is supplied by the control unit UC, the conductor 91 applies between the initiation electrode 84 and the cathode 26 which is grounded via a conductor 103 an oscillating discharge wherefrom results an initiation spark between snap-ring 51 and snap-ring 52. The ionization of the residual gases contained in chamber 78 caused by the initiation spark generates a main spark between point 25 of sample 23 and cathode 26 through discharge of the capacitor battery 73. The plasma travels between anode 23 and cathode 26. It is concentrated in the vicinity of axis 21 of the central opening 43 of the cathode and is visible through the slot 79 provided for the spectrographic analysis.

The insulating material of block 35 is not visible from the plasma and has therefore no effect on the spectrum generated by the sample.

The fourth electrode 66, electrically insulated (or provided with a bias) has a favourable effect on the confinement or concentration of the plasma in the vicinity of the axis. Thus, there is an increase of the luminosity of the plasma, the continuous background remaining at an acceptable level for a quantitative analysis.

It has been established that a niobium electrode acting as a sample shows, after having been subjected to 500 sparks from a spark generator comprising a concentration electrode with an inner diameter of 16 mm, a crater in the center of its frontal end, which is the proof of the axial localization of the plasma.

The electrical features of the supply circuit are chosen such that the duration of the main spark is substantially equal to the duration required for the circulation of the plasma from the anode to the cathode.

The great distance separating the plasma from the area where the initiation sparks are produced prohibits any pollution of the plasma by particles which might be drawn out by said initiation sparks. This absence of pollution is confirmed by the fact which has been established that the metallic ions generated by the initiation sparks are not detected by the spectrograph.

Moreover, one may choose as constituent material for the initiation electrode a pure refractory material which is not present in the alloy to be analysed.

The snap-rings of the initiation electrode and of the cathode preserve their efficiency in spite of a long use.

The optimum distance between the initiation electrode and the cathode is of the order of 1/10 of mm.

With circular snap-rings made from standard refractory metal wires of a diameter of 1.2 mm, for instance in tungsten, more than 10.000 sparks have been generated without any intervention.

The inner diameter of the snap-rings was of 18.4 mm for the initiation electrode and of 15 mm for the cathode.

Replacement of snap-ring 51 and/or snap-ring 52 is carried out quickly and without problems.

Reference is now being made to FIGS. 4 to 7. The chamber 111 which contains sample 23 and cathode 26, the wall 102 of which is coated inside with a gold film and in which vacuum is maintained through a piping 114, is crowned by a chamber 115 containing a battery of capacitors 117. The capacitors 117 are distributed angularly in regular relationship about axis 118 of chamber 115. There is provided for instance six capacitors $117_1 \ldots 117_6$ distributed about axis 118 and a capacitor $117_7$ along said axis. Said capacitors are contained inside a pot 119 made of an insulating material and the bottom 122 of which, provided with an assembly boss 123 for chamber 111, is coated with a conductive plate 124 engaging the lower armature 121 of capacitors 117. Plate 124 is electrically connected with the supply block 83 through a conductor 128. The upper wall 115' of chamber 115 is formed with holes 125, in the same disposition as capacitors 117, and each of said holes can be plugged at will either by an insulating plug 126 carrying a metallic small plate 126', or by a conductive plug 127.

When a plug 127 is in position, it is in engagement with the opposite armature 121 of a capacitor 117. The capacitor is then operative.

If on the other hand it is a plug 126 which is in position, the opposite capacitor 117 is disconnected. The plate 126' electrically connected to the wall of chamber 115 avoids the formation of charges on the surface of insulator 126.

To chamber 111 is coupled a front chamber 130 connected to means for providing vacuum through mouthpiece 131. A guiding rod 132 provided with means for operating the sample carrying clamp 22' and operated from outside by handle 133 provides in association with the means sealing off the communication with chamber 111 the positioning of the sample on its support 22 and its removal.

The apparatus provides the generation of sparks required for a titration of the elements, metallic or not, present in high or very low concentrations in the samples to be analyzed.

In practice, the in vacuo spark generator supplies a ionization degree range from II to VI.

With capacitors of 0.3 $\mu$F and very low self inductance (60.10$^{-9}$ H), a distance of the order of 1 cm has been adopted between the sample anode and the cathode.

With the coaxial arrangement described, the total self inductance of the discharge circuit is comprised between $115 \times 10^{-9}$ H when only one capacitor of the battery is active, and $62 \times 10^{-9}$ H when the seven capacitors mounted in parallel are active.

The period for the oscillations of the current in the plasma is of 1.17 $\mu$s in the first condition (one capacitor), and of 2.27 $\mu$s when the seven capacitors are active. Intermediate values are obtained by making active a number of capacitors comprised between one and seven.

Very important discharge currents may be obtained: for instance, for a loading voltage of 10 kV, a current of 62 kA/$\mu$s is obtained in the plasma when one capacitor only is active, and of 115 kA/μs when the seven capacitors are active.

The expansion speed of the plasma in vacuum being of the order $2.10^6$ cm/second, the invention foresees to obtain a discharge such that the time necessary for the melting, vaporizing and excitation of the plasma be of the same order of magnitude as the time needed for the plasma to cover the distance between the anode and the cathode.

The in vacuo spark generator according to the invention is usable in association with a spectrograph of a large wavelength range, for instance which can vary between 140 and 3200 Å, and a large dispersion (2.5 Å/mm) for studying and using in view of an analysis the spectrum generated by the plasma.

It is established that in spite of the very brief discharge obtained, the line spectrum is perfectly excited and shows lines of the orders II to VI.

The continuous background remains at a level which is acceptable for a quantitative titration of the constituents of the sample.

With ionization degrees varying from II to VI, one may titrate gases (O, N), metalloids and metals in the form of traces or in high concentration.

What is claimed is:

1. An in vacuo spark generator for the spectral analysis in the ultraviolet range of a sample acting as an anode, with, located in a chamber enclosing the sample, a coaxial annular cathode cooperating with the anode and an electrode for the formation of initiation sparks, the operative portion of which is disposed opposite the outer side surface of the cathode and set back relative to the frontal face of the cathode, wherein the cathode frontal face is rounded and the opposite portions of the cathode and the initiation electrode are provided each with removable snap-rings slightly protruding relative to the body of the cathode and initiation electrode, said snap-rings being housed in a semi-circular groove provided in the body of the cathode and the initiation electrode.

2. The spark generator according to claim 1, wherein the snap-rings have a circular cross-section.

3. The spark generator according to claim 2, wherein the snap-rings are housed in a semi-circular groove provided in the body of the cathode and of the initiation electrode respectively.

4. The spark generator according to claim 1, wherein an annular auxiliary electrode acts as a concentration agent on the plasma in the gap between the sample and the cathode.

5. The spark generator according to claim 4, wherein the operative edge of the annular electrode is rounded.

6. The spark generator according to claim 4 or 5, wherein the auxiliary electrode is electrically insulated.

7. The spark generator according to claim 6 wherein said concentration electrode is biased.

8. The spark generator according to claim 4 wherein said concentration electrode is biased.

9. The spark generator according to any one of claims 1 to 3, wherein the initiation electrode is adjustable in position relative to the cathode.

10. An apparatus for forming sparks, comprising an in vacuo spark generator for the spectral analysis in the ultraviolet range of a sample acting as an anode, with, located in a chamber enclosing the sample, a coaxial annular cathode cooperating with the anode and an electrode for the formation of initiation sparks, the operative portion of which is disposed opposite the outer side surface of the cathode and set back relative to the frontal face of the cathode, wherein the cathode frontal face is rounded and the opposite portions of the cathode and the initiation electrode are provided each with removable snap rings slightly protruding relative to the body of the cathode and initiation electrode, said snap-rings being housed in a semi-circular groove provided in the body of the cathode and the initiation electrode; and a capacitor battery being provided for supplying the discharge energy and contained in a chamber immediately adjacent the chamber enclosing the electrodes.

11. The apparatus according to claim 10, wherein the assembly of the two chambers has a coaxial configuration.

12. The apparatus according to claim 10, wherein means are provided for making operative at will a determined number of capacitors of the battery.

13. The apparatus according to claim 12, wherein the capacitors face holes formed in the upper wall of the chamber, conductive plugs are provided for cooperation with said holes in order to provide an electrical connection between the corresponding capacitor and said wall.

14. The apparatus according to claim 12, wherein the capacitors face holes formed in the upper wall of the chamber, and insulating plugs are provided for cooperation with said holes in order to prevent an electrical connection between the corresponding capacitor and said wall.

* * * * *